Figure 1:
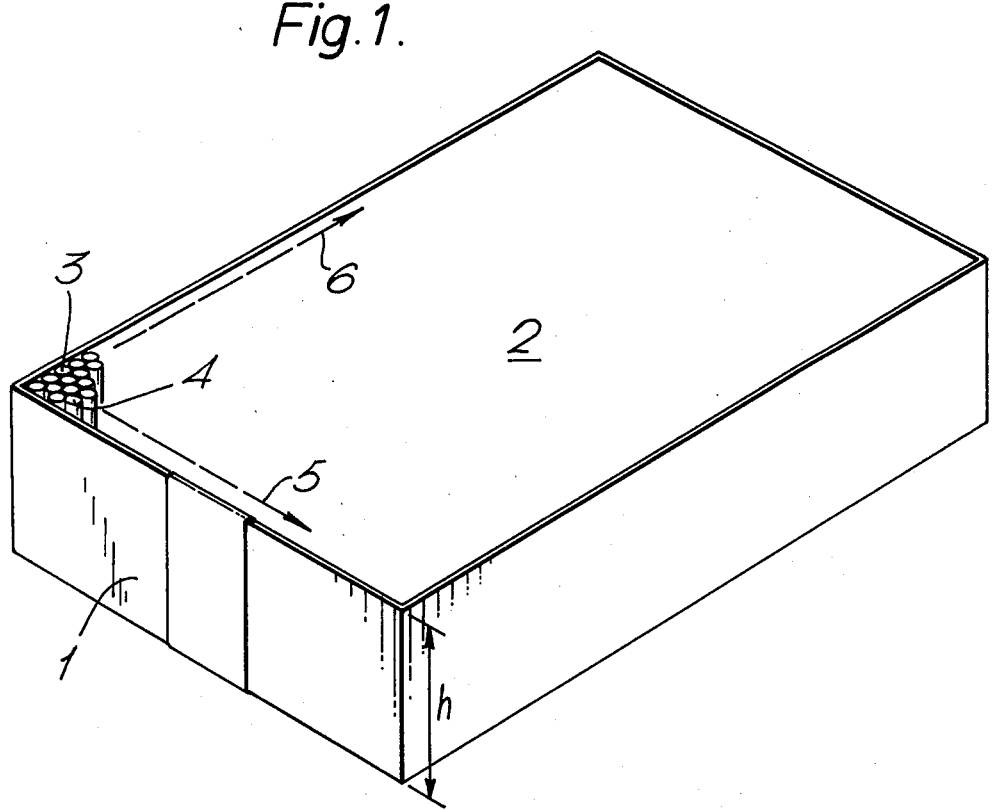

United States Patent [19]

Norman

[11] 4,365,372
[45] Dec. 28, 1982

[54] MATERIALS AND METHODS FOR CULTURE OF NESTING INSECTS

[75] Inventor: Frederick A. Norman, Banksia Park, Australia

[73] Assignee: Internationale Octrooi Maatschappij "Octropa" B.V., Rotterdam, Netherlands

[21] Appl. No.: 197,411

[22] Filed: Oct. 20, 1980

[30] Foreign Application Priority Data

Oct. 25, 1979 [AU] Australia ............................ PE1065

[51] Int. Cl.³ ............................................. A01K 47/00
[52] U.S. Cl. ............................................................. 6/1
[58] Field of Search .......................... 6/1, 2 R, 10, 11; 119/1; 206/443

[56] References Cited

U.S. PATENT DOCUMENTS

| | | | |
|---|---|---|---|
| 2,382,597 | 8/1945 | Amberg | 206/443 X |
| 3,088,135 | 5/1963 | Covington | 6/11 X |
| 3,191,199 | 6/1965 | Barnes, Jr. | 6/11 |
| 3,936,894 | 2/1976 | Barber | 6/11 |
| 4,257,134 | 3/1981 | Niebur | 6/1 |

Primary Examiner—Robert Peshock
Assistant Examiner—Robert P. Swiatek
Attorney, Agent, or Firm—Kramer and Brufsky

[57] ABSTRACT

Nesting insects, e.g. lucerne leaf cutter bees and bumble bees, are cultured in artificial nests comprising assemblies of tubes, e.g. waxed paper tubes, packed with open ends located at the open front of a container e.g. an open waxed paper box. In use the insects fill the tubes with accessory nesting materials e.g. leaf cuttings, nectar, pollen, and with eggs and/or brood. The nests or portions thereof down to individual occupied tubes can be overwintered about 4° C. as long into the season as desired and incubated about 25° C. for 21 to 35 days when desired to synchronize insect emergence with expected crop flowering requiring pollination.

17 Claims, 1 Drawing Figure

U.S. Patent  Dec. 28, 1982  4,365,372

MATERIALS AND METHODS FOR CULTURE OF NESTING INSECTS

This invention concerns materials and methods for culture of nesting insects, such as leaf cutter bees, e.g. as used to effect pollination of plants, in particular field lucernes and clovers. The invention is also applicable to bumble bees, for example.

Many bees in the wild state live in crevices or small holes in trees or dead timber. It has been proposed and tried to provide an artificial nest for use by them as an aid to domestication of them.

In the husbandry of leaf cutter bees, artificial nests have been taken, filled with brood (that is to say eggs and immature bees in individual cells), and placed in cold storage to cause hibernation of the blood. Subsequently when a particular crop of lucerne or clover or the like is about to come into flower the nest is taken from the cold store and allowed to warm up so as to incubate the brood. Shortly thereafter fully developed bees emerge. The bees pollinate the crop, live out their life cycle to produce fresh brood and the process can be repeated.

One such artificial nest comprises a slab of timber with a large number of holes drilled in it.

Preferably, the nesting arrangement should be able to accommodate a large number of bees in a small overall volume, should provide blind-ended tunnels of an appropriate diameter for the bees to inhabit, should be light in weight so as to be readily portable, and should be reasonably waterproof.

According to this invention there is provided a nesting arrangement suitable for nesting insects, e.g. leaf cutter bees or bumble bees, which comprises a container having an open front face and packed therein a plurality of tubes, preferably in sufficient number to fill the container substantially completely. Each tube preferably has one end closed by the rear wall of the container and its other open end exposed at the open front of the container. Preferably the tubes are of fibrous material e.g. paper.

According to preferred embodiments of the invention the outer container may be a waxed cardboard open-fronted carton and the tubes may be lengths of conventional, wound paper, drinking straws which are waxed preferably subsequently to their being packed within the container, and so fixed in place.

The size and shape of the container and tubes are such as to accommodate the insects to be housed. Details are given below in respect of leaf cutter bees and the reader will be easily able to make adjustments in respect of other insects to be housed.

A preferred method of making such a nest is to take a container which is in the form of a cardboard carton with its front wall absent, it may be approximately 350 millimeters long by 280 millimeters high by 120 millimeters thick, pack the container full of unwaxed, wound paper, drinking straws cut to approximately 120 millimeters in length so that the body of straws rests upon the floor of the container with one end of each straw abutting the rear wall of the container and the other end of each straw exposed at the open front of the container, dip the entire ensemble in a waterproofing wax and spin it in a centrifuge to adhere all of the straws together as an integral body and also to adhere that body of straws to the walls of the container. Conventional drinking straws, e.g. about 6 mm (¼ inch) diameter are entirely suitable and the exact diameter, and the depth of straw cavity, typically of the order of 120 mm long, are not limiting.

A small quantity of wax may remain in the bore of each straw at the rear end thereof.

For preference, the paper used in the manufacture of the straws and the cardboard of the carton are a light brown colour to give the impression of timber in the finished product. It will be appreciated however that the colouration is by no means essential to the invention. It will also be appreciated that the dimensions quoted are by way of example, both larger and smaller nests may be made depending upon the requirements of the lucerne or clover grower.

A plurality of nests in accordance with embodiments of the invention can be stacked together in a weather-proof enclosure to form a home or hive for a bee colony in the field.

The present invention may also be applied to nests for other types of bees, for example, large bumble bees, and in that event of course the paper tubes would be of larger diameter, they nevertheless may be made for example in the same way as are the tubes of drinking straws by spirally winding an adhesive coated paper upon a mandrel.

Nests according to the preferred embodiment of the invention are better adapted to the above-mentioned bee husbandry technique than previous artificial nests as they have considerably less thermal capacity than wood and also are able to house considerably more bees in a given overall nest volume.

Furthermore, in the commercial breeding and sale of bees it frequently happens that the customer may not wish to purchase an entire nest of brood but may for example wish only to purchase a relatively small quantity of hibernating brood with the intention of building up his own bee stocks by natural increase and in that event nests according to the above-described embodiment of the invention can be broken apart into individual tubes each with three or four pupae or the like within it for sale or transport in any desired quantity.

FIG. 1 of the accompanying drawing diagrammatically illustrates an embodiment of an artificial nest in accordance with this invention, in fragmentary perspective view.

The FIGURE shows a waxed cardboard open-fronted box 1 having an open front 2 shown largely blank in the FIGURE. Packed within the container 1 are a multiplicity of waxed paper tubes of the form for example of drinking straws, of which a few only are shown in the FIGURE as 3, 4. Straws 3, 4 and their companions are packed into box 1 with open ends located at the open front 2 of box 1. That is, the packed array substantially fills the box 1 by extending in two dimensions in the directions of arrows 5,6. The straws may be largely in close-packed array though this is not critical. The straws and box are waxed after packing so that they form a coherent unit. Height h of the box 1 is about 120 millimeters, and the diameter of straws 3, 4 etc. is about 6 millimeters (about ¼ inch): this embodiment is adapted to the culture of leaf-cutter bees and when in use according to the invention straws of the embodiment are occupied by eggs and/or immature brood of the insects. It is within the scope of the invention to break up such a nest into individual occupied straws or like tubes each occupied by eggs and/or immature brood, for purposes of propagation; and to provide such nests which contain accessory nesting materials such as vegetable matter, e.g. leaf cuttings, pollen and/or nectar, which can be placed therein by the insects and later used by them.

In culturing bees according to this invention, the insects are introduced to nesting arrangements of the kind described above and allowed to deposit eggs in the tubes thereof. Normally the insects also deposit vegetable matter such as leaf cuttings, pollen and/or nectar. Such accessory nesting materials can have been previously provided by earlier conditioning of the nests if desired. The occupied nests are kept to the stage of pupation of the brood and then overwintered, e.g. in cold storage, e.g. at about 4° C. Subsequently they are incubated, e.g. at about 25° C., until the emergence of young adult insects is obtained, e.g. after about 21–35 days of such incubation. Cold storage can be continued as long into the season as emergence of the adults is not yet desired, and warm incubation then started. In this way, emergence of young adults can be synchronised with expected flowering of crop plants to be pollinated, e.g. lucerne or clover. The feature of the nesting arrangements allowing sub-division of assemblies of occupied tubes, if desired down to individual tubes, enables distribution and differential timing of the insects and their emergence, under the control of the cultivator.

I claim:

1. A method of culturing nesting insects, which comprises the steps of:
   introducing the insects to a nesting arrangement comprising a container having an open face and packed with a plurality of tubes each with an end closed by a rear wall of the container and another open end exposed at the open front of the container, the tubes being fixed in place by wax in said container with the closed ends of said tubes closed by wax and the cross-section and length of the tubes being adapted to the nesting requirements of the insects; and
   allowing the insects to deposit therein accessory nesting materials.

2. The method of claim 1 wherein said tubes comprise fibrous material.

3. The method of claim 2 wherein said tubes comprise waxed paper material.

4. The method of claim 3 wherein said tubes are formed from helical paper windings.

5. The method of claim 4 wherein said wax is applied to said helical paper windings within said container by dipping said nesting arrangement into a waterproofing wax and then spinning said nesting arrangement in a centrifuge.

6. The method of claim 1, 2, 3 or 4 wherein said tubes are about 6 millimeters in diameter, said nesting arrangement being adapted for the culture of lucerne leaf cutter bees.

7. The method of claim 1 wherein brood is deposited into said nesting arrangement and then pupated, under winter cold storage conditions, at about 4° C., until emergence is required, and then the nesting arrangement is warm-incubated, at about 25° C., until adult insects emerge.

8. Propagating material for use in the culture of nesting insects, said propagating material comprising a nesting arrangement comprising a container having an open face and packed with a plurality of tubes each with one open end and one end closed by a rear wall of the container, said tubes being fixed in place by wax in said container with the closed ends of said tubes closed by wax, and their cross-section and length being adapted to the nesting requirements of the insects and containing eggs or brood.

9. A method of culturing nesting insects including lucerne leaf cutter bees and bumble bees, which comprises the steps of:
   introducing the insects to a nesting arrangement comprising a container having an open face and packed with a plurality of tubes each with one open end and one end closed by a rear wall of the container, said tubes being fixed in place by wax in said container with the closed ends of said tubes closed by wax, and their cross-section and length being adapted to the nesting requirements of the insects; and
   allowing the insects to deposit therein accessory nesting materials selected from leaf cuttings, pollen, nectar, other vegetable matter, eggs and brood.

10. The method of claim 9 wherein said tubes comprise waxed paper material.

11. The method of claim 9 or 10 wherein said tubes are about 6 millimeters in diameter, said arrangement being adapted for the culture of lucerne leaf cutter bees.

12. A nesting arrangement suitable for nesting insects including lucerne leaf cutter bees and bumble bees, comprising a container having an open face and packed with a plurality of tubes each with one open end and one end closed by a rear wall of the container, said tubes being fixed in place by wax in said container with the closed ends of said tubes closed by wax, and their cross-section and length being adapted to the nesting requirements of the insects.

13. The nesting arrangement of claim 12, wherein said tubes comprise waxed paper material.

14. The nesting arrangement of claim 11 or 12 wherein said tubes are about 6 millimeters in diameter, said arrangement being adapted for the culture of lucerne leaf cutter bees.

15. Apparatus for housing nesting insects comprising:
   a plurality of tubes having a cross-section and length to accommodate the insects to be housed;
   a container for holding the tubes, the container having an open face and a rear wall, each of the tubes having one end closed by being in contact with the rear wall and extending from the rear wall towards the open face; and
   means for adhering the tubes and the container together as an integral body, said means being wax that fixes said tubes in place in said container with the closed ends of said tubes closed by wax.

16. The apparatus of claim 15 wherein the tubes comprise waxed paper material.

17. The apparatus of claim 15 or 16 wherein the tubes are about 6 millimeters in diameter and the apparatus is to accommodate lucerne leaf cutter bees.

* * * * *